United States Patent [19]

Helfet

[11] 4,057,858
[45] Nov. 15, 1977

[54] ELBOW PROSTHESIS

[76] Inventor: Arthur Jacob Helfet, 1917 Trust Bank Centre, Heerengracht, Cape Town, South Africa

[21] Appl. No.: 657,939

[22] Filed: Feb. 13, 1976

[30] Foreign Application Priority Data

Feb. 17, 1975 United Kingdom .................. 6677/75

[51] Int. Cl.² .............................................. A61F 1/24
[52] U.S. Cl. ...................................... 3/1.91; 128/92 C
[58] Field of Search ........................ 3/1.91, 1.9, 1.911, 3/1; 128/92 C

[56] References Cited

U.S. PATENT DOCUMENTS

| 3,696,446 | 10/1972 | Bousquet et al. | 3/1.911 |
| 3,798,679 | 3/1974 | Ewald | 128/92 C |
| 3,852,831 | 12/1974 | Dee | 3/1.91 |
| 3,919,725 | 11/1975 | Swanson et al. | 3/1.91 |

Primary Examiner—Ronald L. Frinks
Attorney, Agent, or Firm—Oblon, Fisher, Spivak, McClelland & Maier

[57] ABSTRACT

A hingeless elbow prosthesis including humeral and ulnar implants, in which the head of the humeral implant has a convex medial condylar formation presenting a smooth curved trochlear groove in the shape of part of a helix and providing a bearing surface for a head of the ulnar implant and in which the ulnar implant presents a condylar head contoured to fit into the trochlear groove, so that as the ulnar implant pivots around the humeral implant, with the condylar head mating with the trochlear groove, the ulnar implant moves along the pivotal axis and the ulnar performs the required valgus in extension and varus in flexion.

8 Claims, 12 Drawing Figures

U.S. Patent  Nov. 15, 1977  Sheet 1 of 2  4,057,858
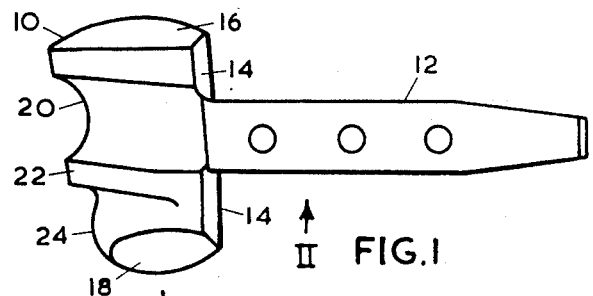
FIG. 1
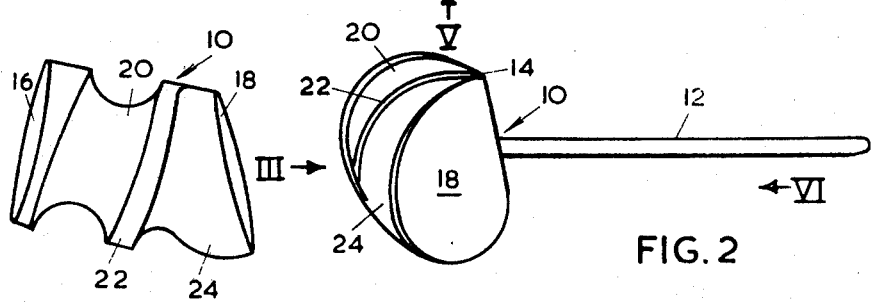
FIG. 2
FIG. 3
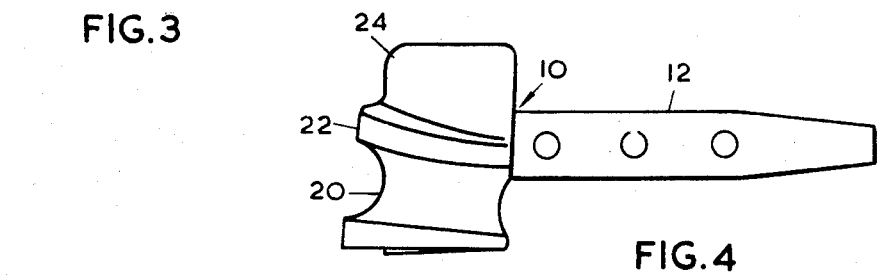
FIG. 4
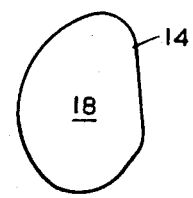
FIG. 5
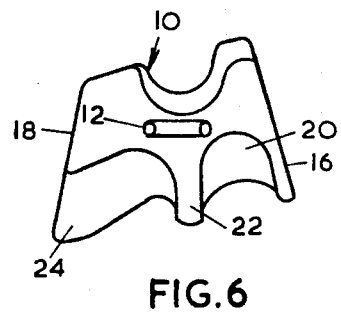
FIG. 6

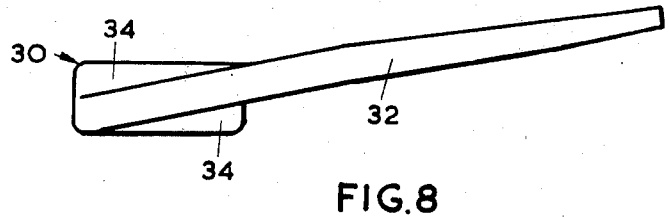
FIG.8
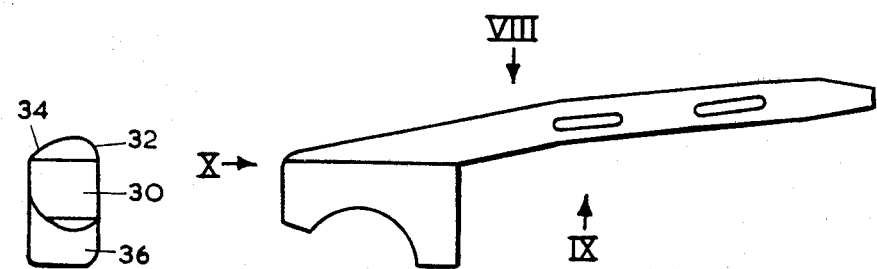
FIG.10  FIG.7
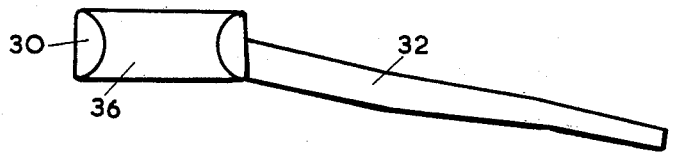
FIG.9
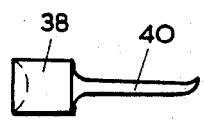  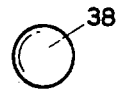
FIG.11  FIG.12

ELBOW PROSTHESIS

BACKGROUND OF THE INVENTION

This invention relates to an elbow prosthesis for implantation to replace a diseased or damaged natural joint. It is designed to reproduce the natural movements of a normal joint with a minimum of surgical excision of bone and the preservation, where possible, of natural muscle attachments.

In a normal human arm, the forearm pivots (assuming no actual rotation) about the humerus in a valgus-varus path. The valgus excursion occurs in extension, when the forearm points away from the body centreline, while the varus excursion occurs in flexion, when the forearm points towards the body centreline.

SUMMARY OF THE INVENTION

The present invention aims at providing an elbow prosthesis which reproduces, with reasonable fidelity, the normal movements of a natural elbow joint while at the same time permitting rotation of the wrist.

Accordingly the present invention provides an elbow prosthesis which is as claimed in the appended claims.

The term "mean hinge axis" in this specification means the axis about which the ulnar implant pivots on the humerus implant when the forearm moves about the upper arm without rotation.

Depending on the degree of damage to the natural joint which it is desired to replace with the prosthesis of the present invention, the prosthesis may include a third implant in the form of a cup of socket adapted to be secured to the top of the radius and having a concave bearing surface adapted to fit snugly against a complementary bearing surface presented by the lateral condyle on the humerus implant.

BRIEF DESCRIPTION OF THE DRAWINGS

The elbow prosthesis of the present invention will now be described, by way of example only, with reference to the accompanying drawings, in which FIG. 1 to 6 show a humerus implant, and FIGS. 7 to 10 show an ulnar implant. In the drawings:

FIG. 1 is an anterior horizontal elevation of the implant for a left-hand humerus;

FIG. 2 is a view seen in the direction of the arrow II of FIG. 1;

FIG. 3 is an end elevation in the direction of the arrow III of FIG. 2;

FIG. 4 is a posterior horizontal elevation of the implant shown in FIG. 1;

FIG. 5 is a view in the direction of arrow V of FIG. 1;

FIG. 6 is an end elevation in the direction of the arrow VI of the FIG. 2;

FIG. 7 is a side elevation of an ulnar implant intended to coact with the humerus implant shown in FIGS. 1 to 6;

FIG. 8 is a view in the direction of the arrow VIII of FIG. 7;

FIG. 9 is a view in the direction of the arrow IX of FIG. 7;

FIG. 10 is a view in the direction of the arrow X of FIG. 7, and

FIGS. 11 and 12 are a side elevation and end view of a radius head implant for optional use with the prosthesis of the invention.

DESCRIPTION OF THE PREFERRED EMBODIMENT

Referring first to the humerus implant shown in FIGS. 1 to 6, a condylar head is secured to a shank or stem 12 which latter is adapted to be inserted into and locked in (for example, by means of surgical cement) the medullary cavity of the humerus. The head 10 has a flat back or upper surface 14 intended to seat firmly on a correspondingly-excised surface of the humerus. Where possible, the medial and lateral margins of the humerus are left intact and the corresponding end walls 16, 18 of the head 10 are machined flat so as to be a snug fit within a groove excised in the distal end or condyles of the humerus, and all three surfaces 14, 16, 18 may be coated with cement so that the implant is as securely anchored in the humerus as possible. Where—for example, in the case of extensive damage to the distal end of the humerus—the lateral margins cannot safely be retained, the end walls, 16, 18 will be contoured as closely as possible to the original contours of the healthy bone.

The medial condyle of the head 10 is both convex to the shank or stem 12 on a circular arc, and is convexly grooved at 20, the groove being of part-circular transverse cross-section. The groove 20 is symmetrical about a radial plane which makes an angle (seen more clearly in FIGS. 4 and 6) with the mean hinge axis such that, when the forearm flexes on the humerus implant 10, without rotation about its own axis, the forearm makes the natural varus excursion.

Separated laterally from the medial condylar groove 20 by a land 22 is a part-spherical lateral condyle, 24 adapted to receive the correspondingly contoured head of the radius. Condyle 24 could be omitted from some forms of the prosthesis. Because there would then be no contact between the humerus implant and the radius, the resultant joint would function, but would be less stable. This would result in the implant being significantly smaller.

Referring now to FIGS. 7-10 which illustrate the ulnar condyle, a head 30 is secured to a shank or steam 32 for providing intra-medullary fixation. The condylar head 30 consists of a flat-sided block from the rear edge 34 of which springs the shank 32. The other or front edge of the head 30 is concave at 36 over the greater part of its extent, this concavity being formed on a mean circular arc and being itself convex in transverse section (as will be appreciated from FIGS. 9 and 10) so as to be a snug pivotal fit in the medial humerus condyle 20. The upper end of the condyle 30 is chamfered to permit the necessary extent of angular flexion of the ulnar implant on the humerus.

The radius head implant shown in FIGS. 11 and 12 is not always required in the fitting of a prosthesis according to the present invention. Should, however, such an implant be required, it will consist of a dished socket 38 spherically contoured on its bearing side to be a snug fit on the lateral humerus condyle 24. Extending from the socket member 38 is an integral fixing shank 40 adapted to be inserted in the medullary cavity of the radius.

The material of the humerus implant 10, 12 will normally be of a biologically-inert metal and should be finished to a high degree of smoothness—preferably polished. The ulnar and, if provided, the radius implant, is best made of wear-resistant, self-lubricating, biologically-inert plastics material. Experience suggests that a high density polyethylene best fulfills this requirement at the present time, having better wear-resistance properties than polytetrafluorethylene whose frictional coefficient is lower by comparison.

It will be understood that the materials for the implants may be interchanged if desired, the humerus implant being of plastics an the other or others of metal.

The actual transverse cross-sectional shapes of the trochlear groove 20 and the coacting ulnar condyle 36 are optional, through an arcuate cross-section is preferred, with the curvatures being complementary.

Although the prosthesis has been shown and described as having each implant fixed to its respective bone by means of a fixing shank or stem of which the dimensions are such as to permit its insertion into the medullary cavity of the respective bone, other methods of fixation may be adopted where appropriate. When a fixing stem is employed, it is normally perforated to enable it to become bonded to the bone by means of surgical cement and by the later growth of natural bone.

Obviously, numerous additional modifications and variations of the present invention are possible in light of the above teachings. It is therefore to be understood that within the scope of the appended claims, the invention may be practiced otherwise than as specifically described herein.

What is claimed as new and desired to be secured by Letters Patent in the United States is:

1. A hingeless elbow prosthesis including humeral and ulnar implants, in which the head of the humeral implant has a convex medial condylar formation presenting a smooth curved trochlar groove in the shape of part of a helix and providing a bearing surface for a head of the ulnar implant, and in which the ulnar implant presents a condylar head contoured to fit into the trochlear groove, so that as the ulnar implant pivots around the humeral implant, with the condylar head mating with the trochlear groove, the ulnar implant moves along the pivotal axis and the ulna performs the required valgus in extension and varus in flexion.

2. An elbow prosthesis as claimed in claim 1, in which the humeral implant also has a convex condylar formation providing a smooth bulbous bearing surface for the head of the radius, or a radius implant.

3. A prosthesis as claimed in claim 1 in which the trochlear groove in the medial condylar formation of the humeral implant has a constant radius in transverse cross-section, and in which the bearing surface in the head of the ulnar implant is concave and of complementary curvature.

4. A prosthesis as claimed in claim 2, including a third implant in the form of a cup or socket adapted to be secured in the top of the radius and having a concave bearing surface adapted to fit snugly against the bearing surface of the medial condylar formation on the humeral implant.

5. A prosthesis as claimed in claim 1, in which at least one of the implants has extending from it a fixing shank adapted to be inserted into the medullary cavity of the respective bone.

6. A prosthesis as claimed in claim 1, in which the humeral implant is of a biologically-inert metal, and in which the ulnar implant is of a biologically-inert plastics material.

7. A prosthesis as claimed in claim 6, in which the plastic material is high-density polyethylene.

8. A prosthesis as claimed in claim 1 wherein the curved surfaces of the trochlear groove of the humeral implant are complementary with the curved surfaces of the condylar head of the ulnar implant.

* * * * *